United States Patent [19]

Krauter et al.

[11] Patent Number: 4,998,182
[45] Date of Patent: Mar. 5, 1991

[54] CONNECTOR FOR OPTICAL SENSOR

[75] Inventors: Allan I. Krauter, Syracuse; Robert L. Vivenzio, Auburn, both of N.Y.

[73] Assignee: Welch Allyn, Inc., Skaneateles Falls, N.Y.

[21] Appl. No.: 476,946

[22] Filed: Feb. 8, 1990

[51] Int. Cl.[5] ............................................... H05K 5/02
[52] U.S. Cl. ........................................ 361/394; 128/4; 128/6; 358/90; 361/380; 439/840
[58] Field of Search ......................... 128/4, 6; 358/98; 361/380, 392, 394, 413, 428; 439/482, 819, 840, 841, 482, 912

[56] References Cited

U.S. PATENT DOCUMENTS

| | | | |
|---|---|---|---|
| 4,688,555 | 8/1987 | Wardle | 128/4 |
| 4,732,156 | 3/1988 | Nakamura | 128/4 |
| 4,805,596 | 2/1989 | Hatori | 128/4 |
| 4,871,229 | 10/1989 | Tashiro | 128/6 |

Primary Examiner—Gregory D. Thompson
Attorney, Agent, or Firm—Wall and Roehrig

[57] ABSTRACT

A connector is provided for a highly miniaturized integrated circuit imager that is supported in a sealed package that has a transparent distal plate and a plurality of connector pins that extend proximally from the package. The connector pins are trimmed short and metal coil springs are disposed on each of these pins. The connector includes tubular sockets mounted onto an elongated ceramic capacitor which serves to smooth power that is applied between the power and ground pins of the imager. A canister is situated over the imager to retain the same with the springs compressed against their respective sockets. Deflectable legs that extend proximally from the canister are bent inward and bound with a coil of fishline or other suitable cord to retain the canister in place.

12 Claims, 2 Drawing Sheets

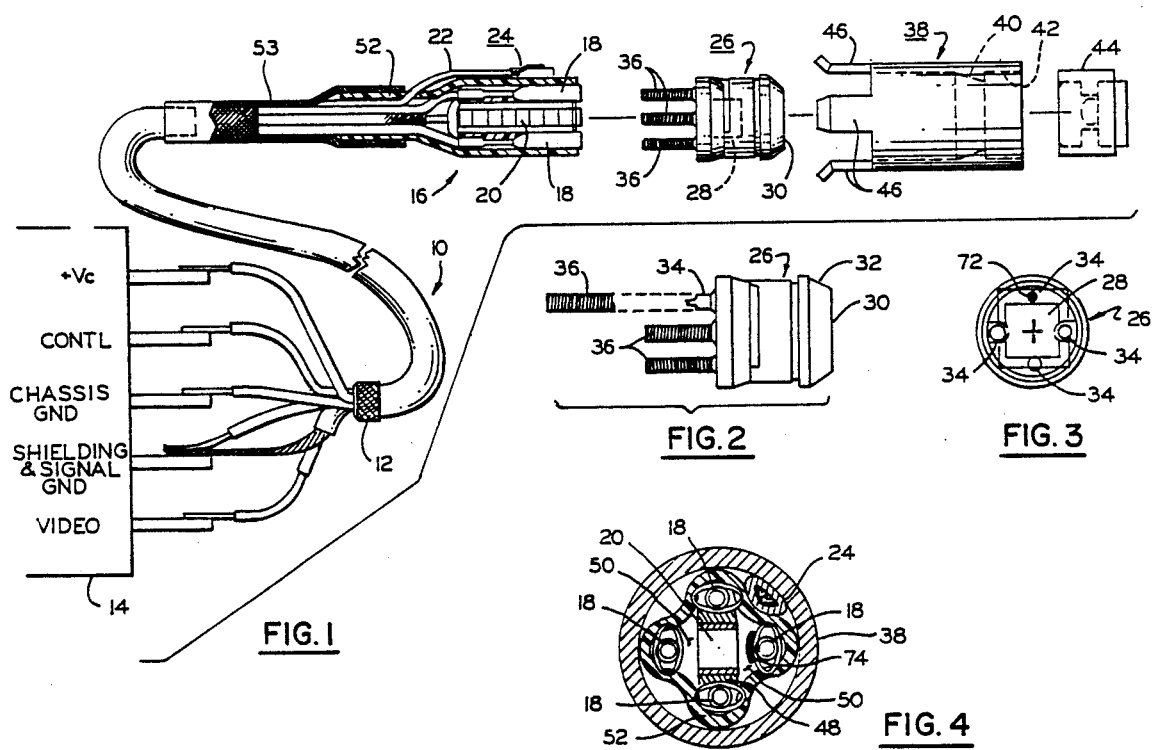

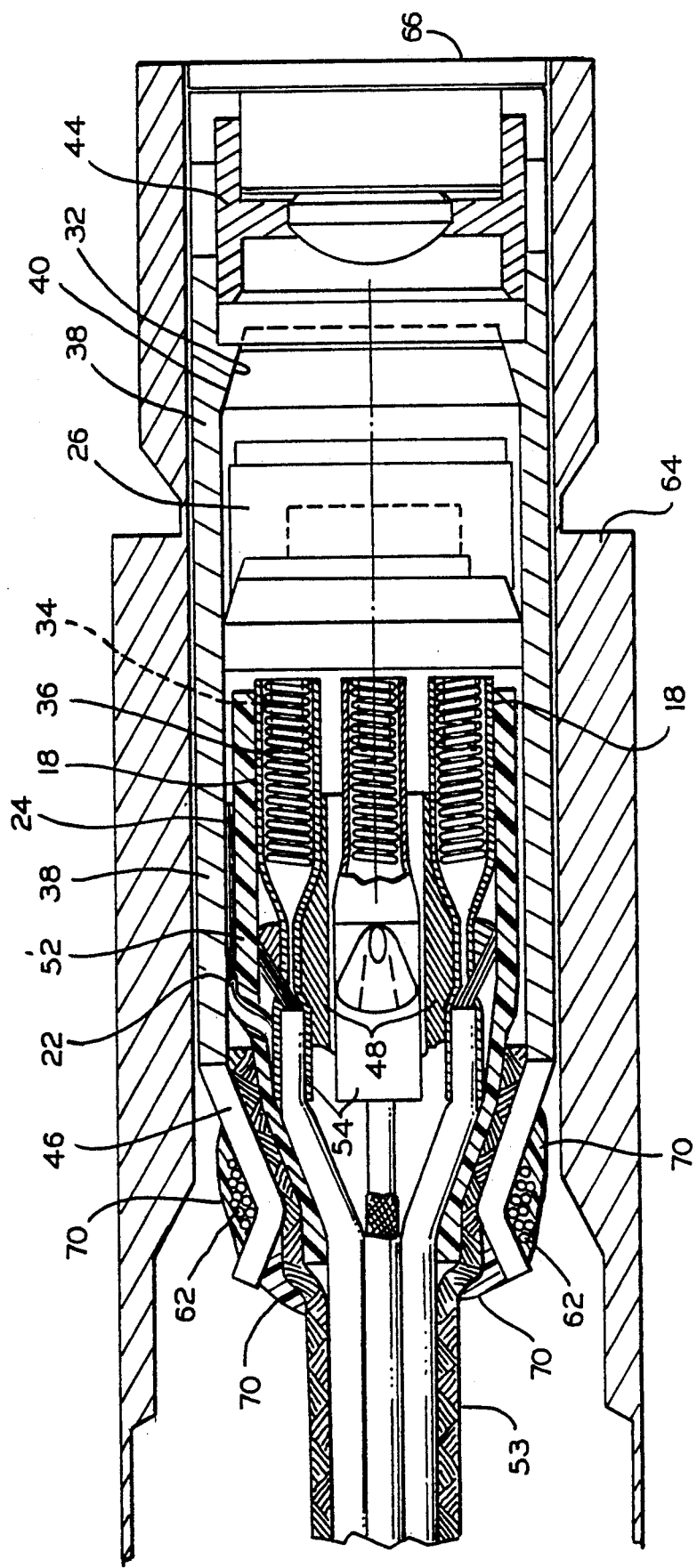

CONNECTOR FOR OPTICAL SENSOR

BACKGROUND OF THE INVENTION

This invention relates to sockets and connectors for modular devices having pin electrodes, and is more particularly directed to a connector for a miniature integrated-circuit video imager, of the type employed in borescopes, endoscopes, or other small video probes.

Highly compact imagers for endoscopes or other probes are formed as charge-coupled devices (CCD's) or other integrated circuits that are packaged or encapsulated with a transparent faceplate through which an image is focused onto an imaging area. Several electrodes protrude from an opposite side of the package, in the form of pin conductors, with pins being provided for power and ground, for control and synch signal input, and for video signal output. A typical image sensor is described in U.S. Pat. No. 4,491,865, granted Jan. 1, 1985. These imagers are available as monochrome or full-color imagers.

Typically, the wiring harness that contains power, ground, control, and signal conductors is attached by soldering the conductors to the respective pins. Then the imager is placed into a canister or housing, and the assembly is potted in epoxy to seal the unit over the conductors.

If it later becomes necessary to disassemble the unit, it is required to soften and remove the epoxy and then remove the solder from the imager pins. This is a difficult operation, and is quite delicate because of the sensitivity of the integrated circuit to heat. As the imagers cost several hundred dollars apiece, the steps of soldering and desoldering involve considerable risk. However, no operative solderless system has been proposed for coupling to the pins of the imager.

Many miniature connectors are available for electronics modules, and some test probes incorporate miniature internal springs. However, there is no known connector that employs springs or the like for connecting to a video module.

OBJECTS AND SUMMARY OF THE INVENTION

It is an object of this invention to provide a reliable, robust electrical connection between the terminal pins of the imager and the wires or conductors of a harness.

It is another object to improve the serviceability of an image sensor by providing means by which the image sensor can be installed or removed without soldering.

It is a further object of the invention to produce an imager assembly of reduced size, both axially and radially.

It is a still further object to provide a connector in which a capacitor is coupled between the ground and power pins of the imager.

It is yet another object of this invention to provide a connector and imager assembly that facilitates construction and manufacture of the imager and harness assembly of a video instrument.

According to an aspect of this invention, a connector couples a wiring harness to a CCD imager of the type that is encased in a housing with connector pins that protrude in a predetermined array from the back or proximal side and has a transparent plate on its front or distal side, through which an image is focused onto an imaging area. There are connector pins for power and ground, for control signal input, and for video signal output. A plurality of metal coil springs are disposed each on a respective one of pins of the imager. The connector includes a plurality of tubular sockets, each of which is connected to a respective conductor of the wiring harness, which is coupled to a remote image processing unit. Each of the tubular sockets has a tubular distal portion to receive the associated spring that is mounted on one of the connector pins, with the sockets being mounted in an array to match that of the pins. In a preferred embodiment the power and ground sockets are soldered to an elongated ceramic capacitor, and the video and control signal sockets are cemented to this capacitor, e.g., with epoxy.

A casing or canister, for example, serves to retain the integrated circuit imager in the connector so that the coil springs are biased against conductive interior surfaces of the respective sockets. A ground wire in the harness terminates at an additional socket which has been flattened. The additional flattened socket is compressed between the canister and a sheath of the connector to establish a ground for the canister. This protects the CCD imaging device from static charge, to which it is rather sensitive.

The canister has a conic interior surface that mates with a chamferred distal rim of the imager to retain the imager in the sockets of the connector. Proximally projecting legs of the canister are deflected inwardly, i.e., towards the axis, and bound up with a coil of fishline or equivalent cord.

The tubular sockets are formed with a transverse slit through which its associated conductor wire end can pass. The wire enters the proximal end of the socket and passes out through the slit, where it is soldered to the exterior of the socket, the proximal end of the socket being crimped onto the wire to establish good mechanical support. A central portion of the socket, just distal of the slot, is flattened to provide space for the solder joint and to establish a surface inside the socket onto which the coil spring of the associated connector pin can be compressed.

With this connector and imager assembly, a robust electrical connection can be established reliably between the imager pins and the harness wire conductors, and the imager can be installed or removed without subjecting it to the heat of soldering. The assembly can be made somewhat shorter than previously, also because the imager pins are not soldered to the harness wire conductors. Moreover, the assembly is extremely compact in the radial direction. The elongated capacitor serves a dual purpose of smoothing the power to the power input and ground pins, and also of mechanically supporting the tubular sockets.

The above and other objects, features and advantages of this invention will be more fully understood from the ensuing description of preferred embodiment, to be read in conjunction with the accompanying Drawing:

BRIEF DESCRIPTION OF THE DRAWING

FIG. 1 is an exploded view of the internal wiring harness of a video probe including an imager and connector assembly according to one embodiment of the present invention.

FIGS. 2 and 3 are side and frontal views of a solid state imager as employed in this embodiment.

FIG. 4 is a cross-section of the connector and canister of this embodiment.

FIGS. 5 and 6 are top and side views of a tubular socket employed in the connector of this embodiment.

FIG. 7 is a cross section of a probe tip of the video probe according to this embodiment of the present invention.

BRIEF DESCRIPTION OF THE PREFERRED EMBODIMENT

With reference to the Drawing, FIG. 1 shows a portion of the internal wiring harness of an elongated flexible video probe of the type which can be incorporated into a video borescope or endoscope that has a miniature video camera assembly disposed at its distal tip.

In this embodiment an elongated wiring harness 10 has a plurality of conductors or wires and a conductive braid encased within a cable sheath 12. The proximal ends of the wires and braid are connected to respective terminals of a video processor 14 to couple to a supply voltage $V_c$, video synchronizing and control signals CONTL, shielding ground and signal ground, and to supply a video signal VIDEO from the imager to the processor.

The distal ends of the wire and braid conductors in the harness 10 terminate at a connector 16, as generally illustrated. As shown also in FIG. 4, the connector has tubular sockets 18 disposed at four longitudinal sides of an elongated capacitor stack 20. The capacitor stack 20 matches the length of the sockets 18. A fifth conductor in the form of a chassis ground wire 22 terminates at an additional, similar socket 24 that has been flattened along its length.

A compact video imager 26, as also shown in FIGS. 2 and 3, has an integrated circuit 28, e.g. a charge coupled device that is encapsulated in the imager package, with a transparent plate 30 at its forward or distal end that permits an image to be focused upon an imaging area of the integrated circuit 28. This plate 30 has a chamfer 32 about its periphery.

There are four connector pins 34 that extend proximally from the imager package 26. These are trimmed short, and each has a respective small coil spring 36 positioned on it. Where the pins 34 are cut short, the metal deforms to produce ears or protuberances that permit the coil springs 36 to be screwed on to the ends of the pins. The inner diameters of the springs are smaller than the outer diameters of the pins; thereby, a tight fit of the springs on the pins is obtained when the springs expand as they are screwed on to the pins.

The pattern of the pins 34 and springs 36 matches the pattern of the sockets 18 of the connector 16. The imager package 26 is connected to the connector 16 by inserting the springs 36 into the respective sockets 18. The proper orientation of the imager package 26 relative to the connector 16 is indicated by a mark 72 on the package and by a corresponding mark 74 on the connector. Then, the imager 26 is held in place by means of a tubular canister 38, which fits over the imager package 26 and the connector 16. This biases the springs 36 against the interior of the sockets 18. A frustoconic annular inner surface portion 40 of the canister 38 abuts against the chamfer 32 of the imager. There is a cylindrical distal inner surface portion 42 that receives a lens assembly 44 that is to be positioned ahead of the imager 26. This is later focused by sliding lens assembly 44 relative to the canister 38. At the proximal end of the canister 38 there are a plurality of legs 46 that continue beyond the proximal end of the connector. These legs 46 are deflectable inward, and can be tied with cord or the like to retain the canister 38 onto the connector and imager assembly.

As shown in more detail in FIG. 4, one oppositely disposed pair of the tubular sockets 18 is soldered onto conductive upper and lower elongated metallized surfaces 48 of the capacitor stack 20 which serve as plates or electrodes. These connector sockets 18, which are shown at the top and bottom in FIG. 4, are associated with the ground and power pins of the imager 26. The two other sockets 18, shown to the left and right in FIG. 4, are secured to sides of the capacitor stack 20 by means of an epoxy 50 or other suitable hardenable nonconductive material. A length of shrink tubing 52 covers the sides of the connector 16, including the sockets 18 and capacitor stack 20 and at least a short distal section of the harness wire. The chassis ground wire 22 branches off through the shrink tubing 52, and another length of flexible tubing 53 overlaps the proximal end of the shrink tubing 52 and the end of the sheath 12 of the wiring harness 10.

As shown in FIGS. 5 and 6, each of the tubular sockets has a cylindrical proximal section 54, into which a respective harness wire is inserted. A transverse slot 56 permits a stripped end of the wire to exit to the exterior of the socket 18 where the wire can be soldered. There is a flattened central section 58 distal of the slot 56 and adjacent to it and an open distal end 60. The flattened portion 58 gradually opens up as it joins the tubular distal end 60, to create a tapered internal 5 surface portion, against which the springs 36 can compress. As shown in FIG. 4, the additional flattened socket 24 nests in an axial fold in the shrink tubing 52 and against an inner wall of the canister 38 when the canister is positioned over the imager and connector assembly. This socket 24 is desirably attached to the outer surface of the shrink tubing 52 with adhesive.

As shown in the assembly view of FIG. 7, the legs 46 of the canister 38 are bent inward proximally of the connector 16, and these are tied down with a coil of fishline 62 or equivalent cording. A sealant such as RTV or epoxy 70 can be placed between canister 38 and tubing 53 to seal the connector and imager assembly from ingress of water or other contamination. Then, an outer cylindrical housing 64 is placed over the canister 38. While not shown here, a fiber optic bundle is fanned out and is situated in an annulus between the canister and the housing. This fiber optic bundle provides illumination out the forward or distal end of the probe. A faceplate 66 can be situated in advance of the lens assembly 44. This particular cylindrical housing illustrated in FIG. 7 is adapted to a hooking cap as described in the copending U.S. Patent Application Ser. No. 451,016, filed Dec. 15, 1989, and having a common assignee herewith. The overall diameter of the housing can be on the order of 6 mm or less.

Because the electrical connection between the wires of the harness 10 and the pins 34 of the imager 26 are made without direct soldering, there is no danger of heat damage to the imager 26, either on installation or on removal. Also, because neither soldering nor desoldering is required for installation or removal, the pins 34 are significantly shorter than was the case in the prior art. In fact, the entire imager and connector assembly as shown here is considerably shorter than what would be required where long imager leads are directly soldered to the harness wires and are then encapsulated. Also, because of the incorporation of the capacitor stack 20 into the connector 16, and directly onto the sockets 18, there is considerable smoothing of power applied to the imager 16, and consequently a higher quality picture.

To remove the imager 26, it is necessary only to sever the fishline 62, and then, after bending the legs 46 outwardly, to slide the canister 38 off. The imager 26 can then be removed and replaced, as need be.

While this invention has been described in detail with respect to a preferred embodiment, it should be understood that the invention is not limited to that precise embodiment. Rather, many modifications and variations would present themselves to those skilled in the art without departing from the scope and spirit of this invention, as defined in the appended claims.

What is claimed is:

1. An imager and connector assembly comprising
an integrated-circuit imager supported in a package having a transparent distal plate and a plurality of connector pins that extend proximally from the package in a predetermined array, the connector pins including a pair of power pins to which electrical power is supplied, a video signal output pin, and a control signal input pin;
a connector connecting the imager to a plurality of conductors carrying electrical power and control signals to said imager and carrying video signals from said imager to a video signal processor; the connector including a plurality of metal coil springs each disposed on a respective one of the pins of said imager, a plurality of tubular sockets each connected to a respective one of said conductors and having a tubular distal portion to receive the springs mounted on the pins of said imager, and means mounting said tubular sockets in a predetermined array to match that of said connector pins; and
means retaining said integrated circuit imager in said connector so that said coil springs are biased against conductive surfaces of their associated sockets.

2. The imager and connector assembly of claim 1 wherein the connector has a pair of said sockets disposed radially opposite one another, and includes an elongated capacitor extending axially between said pair of sockets with said pair of sockets soldered onto oppositely disposed electrodes of said capacitor.

3. The imager and connector assembly of claim 2 wherein said capacitor is an elongated ceramic capacitor and said electrodes thereof are axially elongated metallized surfaces thereon.

4. The imager and connector assembly of claim 3 wherein said connector has a second pair of said sockets supported on additional axially elongated surfaces of said capacitor.

5. The imager and connector assembly of claim 4, said connector further including a sheath of shrink tubing over the first mentioned and second pairs of sockets and said capacitor.

6. The imager and connector assembly of claim 5 wherein said means retaining the imager in said socket includes a tubular conductive canister disposed over said connector and said imager, and said connector further includes an additional socket coupled to a grounding conductor and situated between the sheath of shrink tubing and the canister.

7. The imager and connector assembly of claim 1 wherein said imager package distal plate has a chamferred peripheral edge, and said canister has a conic surface portion positioned distally on its interior and on which said chamferred peripheral edge is seated.

8. The imager and connector assembly of claim 7, wherein said canister has a plurality of deflectable legs extending axially at a proximal end of the canister and which are drawn toward the axis and secured over a proximal end of said connector.

9. The imager and connector assembly of claim 8, further comprising a coil of fish line on said legs and binding them.

10. The imager and connector assembly of claim 9, in which said conductors are contained within a wiring harness and a sealant of RTV or epoxy is placed between the deflectable legs and said wiring harness to prevent ingress of water or other contaminants.

11. The imager and connector assembly of claim 1, wherein each said tubular socket has a transverse slit through which its associated conductor is to pass, so that an end of the associated conductor enters the proximal end of the respective socket and exits through the respective transverse slit with a proximal end of the respective socket being crimped onto the associated conductor for mechanical support and the end of the associated conductor outside the respective transverse slit being soldered to an exterior surface of the associated socket.

12. The imager and connector assembly of claim 11, wherein a central portion of each said tubular socket is flattened to provide that tubular socket with both an exterior surface with space for soldering the associated conductor and an internal surface against which the coil spring on the associated connector pin can be compressed.

* * * * *